United States Patent [19]

Drewlow

[11] Patent Number: Plant 6,435

[45] Date of Patent: Nov. 29, 1988

[54] BEGONIA PLANT NAMED GUINEVERE

[75] Inventor: Lyndon W. Drewlow, Ashtabula, Ohio

[73] Assignee: Mikkelsens, Inc., Ashtabula, Ohio

[21] Appl. No.: 20,763

[22] Filed: Mar. 2, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Begonia plant named Guinevere, characterized by its pink flower color; double flower form; cyme inflorescence; upright growth with strong stems and good branching; early flowering; and ease of propagation both from stem and leaf cuttings.

1 Drawing Sheet

The present invention relates to a new and distinctive cultivar of Begonia plant, botanically known as *Begonia hiemalis,* Fotsch, and known by the cultivar name Guinevere.

The new cultivar was discovered by me as a seedling from a controlled crossing of *B. tuberhybrida,* Mikkelsen Seedling No. 84-613-5, as the seed parent with *B. socotrana,* Mikkelsen Seedling No. 84-1019-6, as the pollen parent.

Asexual reproduction by stem and/or leaf cuttings by me at Ashtabula, Ohio, has reproduced the unique features of the new cultivar through successive propagations.

The following characteristics distinguish the new begonia from both its parents and other begonias commercially known and used in the floriculture industry. In describing Guinevere, comparisons have been made with other cultivars, including Aphrodite Pink (U.S. Plant Pat. No. 3,318), Whisper-of-Pink (U.S. Plant Pat. No. 3,787), Tango (U.S. Plant Pat. No. 5,538), Connie (U.S. Plant Pat. No. 5,169) and St. Helena, an application for which is pending.

1. Guinevere has a distinct light pink flower, with Aphrodite Pink being bright pink, Whisper-of-Pink a more salmon pink, and Tango a salmon orange.

2. The size and round shape of the flower of Guinevere is similar to Tango and St. Helena, with Connie having a smaller flower that is more oblong in shape. Aphrodite Pink has a more ruffled flower.

3. Guinevere has a large, very double flower, similar to St. Helena, Tango and Connie, with Aphrodite Pink being less double and Whisper-of-Pink single.

4. Flower inflorescence is a cyme which is similar to Whisper-of-Pink, while all the other comparison cultivars have a raceme type of inflorescence.

5. Plant height, shape and branching are very similar to Connie. Whisper-of-Pink is taller and St. Helena more compact. Aphrodite Pink is a more spreading plant and Tango is much more compact.

6. Guinevere has strong stems with an upright growth habit similar to Whisper-of-Pink, Connie and St. Helena. Aphrodite Pink and Tango have weaker stems that bend when they get several flowers open.

7. Leaf size of Guinevere is smaller than Whisper-of-Pink, similar to Connie, St. Helena and Aphrodite Pink, and larger than Tango.

8. Leaf color of Guinevere is similar to Connie, Tango and St. Helena, with Aphrodite Pink and Whisper-of-Pink having lighter, brighter green leaves.

9. Guinevere has a red margin and a red tinge into the leaf area of the underside of an immature leaf similar to Tango, Aphrodite Pink and Connie. However, Connie has no red margin and Aphrodite Pink has a fainter red margin. Whisper-of-Pink has a faint red margin but no red in leaf area, and St. Helena has a heavy red margin and more red in underside of leaf.

10. Early flowering nature.

11. Good branching from base of plant after a pinch.

12. Easy to propagate both from stem and leaf cuttings.

13. Strong, upright, floriferous growth habit makes it ideal for 15 and 25 cm pot plant production.

The accompanying colored photograph illustrates in perspective view the overall appearance of Guinevere, showing the colors as true as it is reasonably possible to obtain in a colored reproduction of this type.

The following is a detailed description of Guinevere based on plants produced under commercial practices in Ashtabula, Ohio, under greenhouse conditions. The photograph was taken in early June, 1986, and color references are made to The Royal Horticultural Society Colour Chart except where general color terms of ordinary dictionary significance are used.

Parentage: A controlled cross between *B. tuberhybrida,* Mikkelsen Seedling No. 84-613-5×*B. socotrana,* Mikkelsen Seedling No. 84-1019-6.

Propagation:

(A) *Type cutting.*—Leaf.

(B) *Time to root.*—18 days at 21° C. summer; 24 days at 21° C. winter.

(C) *Rooting habit.*—Numerous, fine, fibrous.

(D) *Time for shoot development.*—10 weeks in summer to 13 weeks in winter to obtain shoots 4 to 5 cm long in length.

Plant description:

(A) *Form.*—Upright, excellent stem strength, good branching after a pinch on stem cuttings; semi-compact, intermediate internodes, full flower cluster, best for 15 and 25 cm pot production.

(B) *Habit of growth.*—Upright with good branching after pinching from base of branch. Early flowering and vigorous; usually vegetative shoots are formed at the basal nodes and flower shoots at the higher nodes.

(C) *Foliage.*—Leaves simple, alternate, borne on strong petioles 6–7 mm in diameter on mature leaves at base of plant. (1) Size: Can vary greatly with leaf position on plant and number of shoots per plant. Environment can also affect leaf size; 11 to 12 cm across on mature basal leaves. (2) Shape: Ovate to almost orbicular on mature leaves. Lobes overlap on immature and mature leaves. (3) Texture: Leathery, glabrous. (4) Margin: Serrated. (5) Color: Young foliage, top side 146A; red tint at margins; Young foliage, under side 147C; reddish cast to entire back except for veins. Mature foliage, top side 147A; Mature foliage, under side 148C. (6) Venation: Palmate, 5–6 major veins.

Flowering description:

(A) *Flowering habits.*—Flowering in a cyme (between a simple and compound dichasium in form), with number of flowers in a cyme being variable. Flowering continues more or less indefinitely, with many flowers open at once.

(B) *Natural flowering season.*—Will flower year around without controlling day length. Plants will flower earlier and more abundantly if subjected to a reduced day length of 12 hours.

(C) *Flower buds.*—20 mm wide and 15 mm long just before opening. Tepals are entire around margins. Color 47C just before opening and 47B when immature.

(D) *Flowers borne.*—On strong, upright peduncles reddish pink in color with pedicels being deeper red in color. Major peduncles are 4 to 5 mm in diameter.

(E) *Quantity.*—Average of 3 to 5 flowers per peduncle, opening in sequence as cyme develops. Several flowering shoots will be open at the same time.

(F) *Tepals.*—(1) Shape: Flat and nearly rounded. (2) Color top and underside in summer when opening: between 48 B and C, fading to 54D; underside 54D. (3) Number of tepals: 40 or more as flower is very double. (4) Size of tepals: 30 mm long and 40 mm wide on first flowers. (5) Flower size: 60 mm in diameter first flowers.

(G) *Reproductive organs.*—(1) Stamens: None as plant is full double with anthers appearing as petals. (2) Pistils: A few female flowers develop on plant. (a) Stigma shape: Curled — 3, color yellow. (b) Style color: Yellow. (c) Ovaries: Numerous; size is 8 mm long, 14 mm wide and 3 lobed; color green with red tint.

Disease resistance: Guinevere has shown good resistance to powdery mildew. No other disease or insect problems observed to date.

I claim:

1. A new and distinct cultivar of Begonia plant named Guinevere, as described and illustrated, and particularly characterized by its pink flower color, double flower form, cyme inflorescence, upright growth with strong stems and good branching, early flowering, and ease of propagation both from stem and leaf cuttings.

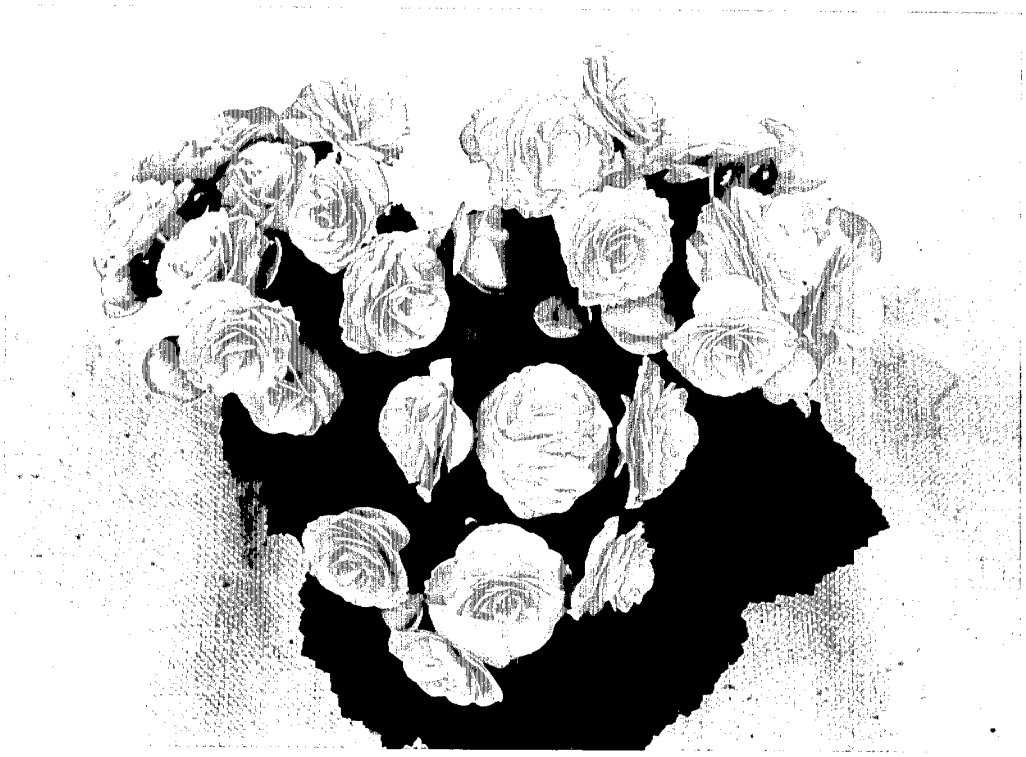

* * * * *